US005610018A

United States Patent [19]
Di Fiore et al.

[11] Patent Number: 5,610,018
[45] Date of Patent: Mar. 11, 1997

[54] SUBSTRATE FOR THE EPIDERMAL GROWTH FACTOR RECEPTOR KINASE, ANTIBODIES THERETO AND METHODS OF USE THEREOF

[75] Inventors: Pier P. Di Fiore, Bethesda, Md.; Francesca Fazioli, Ancona, Italy

[73] Assignee: The United States of America as represented by the Department of Health and Human Services, Washington, D.C.

[21] Appl. No.: 368,079

[22] Filed: Jan. 3, 1995

Related U.S. Application Data

[62] Division of Ser. No. 935,311, Aug. 25, 1992, Pat. No. 5,378,809.
[51] Int. Cl.$^6$ ............................ G01N 33/53; C07K 16/24
[52] U.S. Cl. .................. 435/7.1; 530/387.9; 530/388.24; 530/389.2
[58] Field of Search ............................ 530/387.1, 387.9, 530/388.1, 388.24, 389.2, 350; 435/7.1

[56] References Cited

PUBLICATIONS

I. Fazioli et al. J Biol Chem 267: 5155–5161 (1992).

Aaronson, S., "Growth Factors and Cancer" Science 254: 1146–1153 (Nov. 22, 1991).

Anderson, D., et al., "Binding of SH2 Domains of Phospholipase Cγ1, GAP and Src to Activated Growth Factor Receptors", Science 250: 979–981 (Nov. 16, 1990).

Broek, D., et al., "The S. cerevisiae CDC25 Gene Product Regulates the RAS/Adenylate Cyclase Pathway", Cell, 48: 789–799 (Mar. 13, 1987).

Cleveland, D., W., et al., "Peptide Mapping by Limited Proteolysis in Sodium Dodecyl Sulfate and Analysis by Gel Electrophoresis", J. Biol. Chem. 252(3): 1102–1106 (Feb. 10, 1977).

Coughlin, S., R., et al., "Role of Phosphatidylinositol Kinase in PDGF Receptor Signal Transduction", Science 243: 1191–1194 (Mar. 3, 1989).

Drubin, et al., "Homology of a yeast actin–binding protein to signal transduction proteins and myosin–1", Nature 343: 288–290 (Jan. 18, 1990).

Escobedo, J., A., et al., "A Phoshphatidylinositol–3 Kinase Binds to Platelet–Derived Growth Factor Receptors through a Specific Receptor Sequence Containing Phosphotyrosine", Mol. Cell. Biol. 11(2): 1125–1132 (Feb. 1991).

Escobedo, J., A., et al., "cDNA Cloning of a Novel 85kd Protein that has SH2 Domains and Regulates Binding of PI3–Kinase to the PDGF–βReceptor", Cell 65: 75–82 (Apr. 5, 1991).

Fazioli, F. et al., "The *erb*B–2 Mitogenic Signaling pathway: Tyrosine Phosphorylation of Phospholipase Cγ and GTPase–Activating Protein Does Not Correlate with *erb*B–2 Mitogenic Potency", Mo. Cell. Biol. 11(4): 2040–2048 (Apr. 1991).

Fazioli, F., et al., "Identification and Biochemical Characterization of Novel Putative Substrates for the Epidermal Growth Factor Receptor Kinase", J. Biol. Chem. 267(8): 5155–5161 (Mar. 15, 1992).

Felgner, P., L., et al., "Gene therapeutics", Nature 349: 351–352 (Jan. 24, 1991).

Giard, D., J., et al., "In Vitro Cultivation of Human Tumors: Establishment of Cell Lines Derived From a Series of Solid Tumors", J. Natl. Cancer Inst. 51(5): 1417–1423 (Nov. 1973).

Gomez–Marquez, J., et al., "Prothymosin α is a nuclear protein", FEBS Letters 226(2): 217–216 (Jan. 1988).

Gould, K., L., et al., "Platelet–Derived Growth Factor Induces Multisite Phosphorylation of pp60$^{c-src}$ and Increases its Protein Tyrosine Kinase Activity", Mol. Cell. Biol. 8(8): 3345–3356 (Aug. 1988).

Green, P., J., et al., "The Role of Antisense RNA in Gene Regulation", Ann. Rev. Biochem. 55: 569–597 (1986).

Higuchi, R., "Recombinant PCR" Chapter 22 in PCR Protocols: A Guide to Methods and Applications, pp. 171–183 (1990).

Hughes, D., A., et al., "Homologous sctivators of ras in fission and budding yeast", Nature 344: 355–357 (Mar. 22, 1990).

Jung, G., et al., "The heavy chain of Acanthamoeba myosin IB is a fusion of myosin–like and non–myosin–like sequences", Proc. Natl. Acad. Sci., USA 84: 6720–6724 (Oct. 1987).

Kaplan, D., R., et al., "PDGF β–Receptor Stimulates Tyrosine Phosphorylation of GAP and Association of GAP with a Signaling Complex", Cell 61: 125–133 (Apr. 6, 1990).

Kazlauskas, A., et al., "Autophosphorylation of the PDGF Receptor in the Kinase Insert Region Regulates Interactions with Cell Proteins", Cell 58: 1121–1133 (Sep. 22, 1989).

Kazlauskas, A., et al., "Binding of GAP to Activated PDGF Receptors", Science 247: 1578–1581 (Mar. 30, 1990).

Kirkness, E., F., et al., "Isolation, Characterization, and Localization of Human Genomic DNA Encoding the β1 Subunit of the GABA$_a$ Receptor (GABRB1)", Genomics 10: 985–995 (1991).

Kitamura, D., et al., "Isolation and characterization of a novel human gene expressed specifically in the cells of hematopoietic lineage", Nucleic Acids Res. 17(22): 9367–9379 (1989).

Koch, C., A. et al., "SH2 and SH3 Domains: Elements That Control Interactions of Cytoplasm Signaling Proteins" Science 252: 668–674 (May 3, 1991).

(List continued on next page.)

*Primary Examiner*—Christina Y. Chan
*Assistant Examiner*—Phillip Gambel
*Attorney, Agent, or Firm*—Knobbe, Martens, Olson & Bear

[57] ABSTRACT

A new substrate of epidermal growth factor receptor and other tyrosine kinase receptors denominated eps8, polynucleotide encoding eps8, antisense eps8 polynucleotide, antibodies to eps8, and assays for determining eps8.

7 Claims, No Drawings

OTHER PUBLICATIONS

Kraus, M., H., et al., "[46] Detection and Isolation of Novel Protein–Tyrosine Kinase Genes Employing Reduced Stringency Hybridization", Methods in Enzymology 200: 546–557 (1991).

Kypta, R. M., et al., "Association between the PDGF Receptor and Cell" 62: 481–492 (1990).

Leto, et al., "Cloning of a 67 kD Neutrophil Oxidase Factor with Similarity to a Noncatalytic Region of $p60^{c-src}$", Science 248: 727–730 (May 11, 1990).

Margolis, et al., "EGF Induces Tyrosine Phosphorylation of Phospholipase C–II: A Potential Mechanism for EGF Receptor Signaling", Cell 57: 1101–1107 (Jun. 30, 1989).

Margolis, et al., "The tyrosine phosphorylated carboxyterminus of the EGF receptor is a binding site for GAP and PLC–γ", The EMBO Journal 9(13): 4375–4380 (1990).

Matsuda, et al., "Binding of Transforming Protein $p47^{gag-crk}$, to a Broad Range of Phosphotyrosine–Containing Proteins", Science 248: 1537–1539 (Jun. 22, 1990).

Mayer, et al., "Association of the v–crk oncogene product with phosphotyrosine–containing proteins and protein kinase activity", Proc. Natl. Acad. Sci. USA 87: 2638–2642 (Apr. 1990).

Meisenhelder, et al., "Phospholipase c–γ Is a Substrate for the PDGF and EGF Receptor Protein–Tyrosine Kinases In Vivo and In Vitro", Cell 57: 1109–1122 (Jun. 30, 1989).

Miki, et al., "Expression cDNA Cloning of the KGF Receptor by Creation of a Transforming Autocrine Loop", Science 251: 72–75 (Jan. 4, 1991).

Molloy, et al., "PDGF induction of tyrosine phosphorylation of GTPase activating protein", I Nature 342: 711–714 (Dec. 7, 1989).

Moran, et al., "Src homlogy region 2 domains direct protein–protein interactions in signal transduction", Proc. Natl. Acad. Sci., USA 87: 8622–8626 (Nov. 1990).

Morrison, D., K., et al., "Platelet–Derived Growth Factor (PDGF)–Dependent Association of Phospholipase C–γ with the PDGF Receptor Signaling Complex" Mol. Cell. Biol. 10(5): 2359–2366 (May 1990).

Morrison, D., K., et al., "Direct Activation of the Serine/Threonine Kinase Activity of Raf–1 through Tyrosine Phosphorylation by the PDGF β–Receptor", Cell, 56: 649–657 (Aug. 25, 1989).

Morrison, D., K., et al., "Signal transduction from membrane to cytoplasm: Growth factors and membrane–bound oncogene products increase Raf–1 phosphorylation and associated protein kinase activity", Proc. Natl. Sci, USA 85:8855–8859 (Dec. 1988).

Otsu, M., et al., "Characterization of Two 85 kd Proteins That Associate with Receptor Tyrosine Kinases, Middle–T/$pp60^{c-src}$ Complexes, and PI3–Kinase", Cell 65:91–104 (Apr. 5, 1991).

Rossi, J., J., et al., "The Potential Use of Catalytic RNAs in Therapy of HIV Infection and Other Diseases", Pharmac. Ther. 50: 245–254 (1991).

Ruderman, N., B., et al., "Activation of phosphatidylinositol 3–kinase by insulin", Proc. Natl. Acad. Sci., USA 87: 1411–1415 (Feb. 1990).

Segatto, O., et. al., "The Juxtamembrane Regions of the Epidermal Growth Factor Receptor and $gp185^{erbB-2}$ Determine the Specificity of Signal Transduction", Mol. Cell. Biol. 11(6): 3191–3202 (Jun. 1991).

Skolnik, E., Y., et al., "Cloning of PI3 Kinase–Associated p85 Utilizing a Novel Method for Expression/Cloning of Target Proteins for Receptor Tyrosine Kinases", Cell 65: 83–90 (Apr. 5, 1991).

Trueheart, J., et al., "Two Genes Required for Cell Fusion during Yeast Conjugation: Evidence for a Pheromone–Induced Surface Protein". Mol. Cell. Biol. 7(7): 2316–2328 (Jul. 1987).

Ullrich, A., et al., "Signal Transduction by Receptors with Tryosine Kinase Activity", Cell 61: 203–212 (Apr. 20, 1990).

Varticovski, L., et al., "The colony stimulating factor–1 receptor associates with and activates phosphatidylinositol–3 kinase", Nature 342: 699–702 (Dec. 7, 1989).

Wahl, M., I., et al., "Platelet–Derived Growth Factor Induces Rapid and Sustained Tyrosine Phosphorylation C–γ in Quiescent BALB/c 3T3 Cells", Mol. Cell. Biol. 9(7): 2634–2943 (Jul. 1989).

Wasenius, V., et al., "Primary Structure of the Brain α–Spectrin", J. Cell. Biol. 108:79–93 (Jan. 1989).

Wolff, et al., "Direct Gene Transfer in Mouse Muscle in Vivo" Science 247: 1465–1468 (Mar. 23, 1990).

Tavare, J., M., et al., "Epidermal growth factor, but not insulin, stimulates tyrosine phosphorylation of an endogenous protein of $M_r$ 95000 in Triton extracts of human placental syncytiotrophoblast membranes", Biochem. J. 244: 769–774 (Jun. 15, 1987).

Rothenberg, P., L., et al., "Purification and Partial Sequence Analysis of pp185, the Major Cellular Substrate of the Insulin Receptor Tyrosine Kinase", J. Biol. Chem. 266: 8302–8311 (May 5, 1991).

Leonard, W., J., et al., "Molecular cloning and expression of cDNAs for the human interleukin–2 receptor", Nature 311: 626–631 (Oct. 18, 1984).

Fazioli, F., et al., "Eps8, a substrate for the epidermal growth factor receptor kinase, enhances EGF–Dependent mitogenic signals", The EMBO Journal 12(10): 3799–3808 (1993).

SUBSTRATE FOR THE EPIDERMAL GROWTH FACTOR RECEPTOR KINASE, ANTIBODIES THERETO AND METHODS OF USE THEREOF

This application is a is a divisional of application Ser. No. 07/935,311, filed Aug. 25,1992, now U.S. Pat. No. 5,378, 809.

BACKGROUND OF THE INVENTION

The present invention relates to substrates for the epidermal growth factor receptor kinase, polynucleotide encoding those substrates, and methods for using the substrates.

The cellular machinery involved in mitogenesis is complex, and not fully understood. In general, receptors present on the cell surface bind growth factors, resulting in an activated receptor. In particular, the receptors of interest are endowed with intrinsic tyrosine kinase activity, and are known as tyrosine kinase receptors or TKRs. The activated receptors, in turn, phosphorylate intracellular substrates. These phosphorylated substrates are responsible for a series of events that leads to cell division. This process is generally referred to as "mitogenic signal transduction." The molecular machinery involved in this process is considered to be the "mitogenic signaling pathway."

Growth factors and hormones exert pleiotropic effects on cellular functions, including mitogenic stimulation and modulation of differentiation and metabolism (Ullrich, et al. *Cell* 61: 203–212 (1990); Aaronson, S. A. *Science* 254: 1146–1153 (1991)). In many cases, these actions are mediated by the interaction of growth factors with cell surface tyrosine kinase receptors (TKRs), which results in enhanced receptor catalytic activity and tyrosine phosphorylation of intracellular substrates (Ullrich, et al., supra, Aaronson, supra). Knowledge of the nature of these second messenger systems is still scanty, although some molecules which associate and/or are tyrosine phosphorylated by TKRs have been identified. These include the γ isozyme of phospholipase C (PLC-γ) (Margolis, et al. *Cell* 57:1101–1107 (1989), Meisenhelder, et al. *Cell* 57:1109–1122 (1989) and Wahl, et al. *Mol. Cell. Biol.* 9: 2934–2943 (1989)); the p21ras GTPase activating protein (GAP) (Molloy, et al. *Nature* 342: 711–714 (1989), Kaplan, et al. *Cell* 61: 125–133 (1990), and Kazlauskas, et al. *Science* 247: 1578–1581 (1990)); the raf serine-threonine kinase (Morrison, et al. *Proc. Natl. Acad. Sci. USA* 85: 8855–8859 (1988), and Morrison, et al. Cell 58: 649–657 (1989)); the p85 subunit of the phosphatidylinositol 3-kinase (PtdIns-3K); (Coughlin, et al. *Science* 243: 1191–1194 (1989), Kazlauskas, et al. *Cell* 58: 1121–1133 (1989), Varticovski, et al. *Nature* 342: 699–702 (1989), Ruderman, et al. *Proc. Natl. Acad. Sci. USA* 87: 1411–1415 (1990), Escobedo, et al. *Cell* 65: 75–82 (1991), Skolnik, et al. *Cell* 65: 83–90 (1991), Otsu, et al. Cell 65: 91–104 (1991)) and some cytoplasmic tyrosine kinases (Gould, et al. *Mol. Cell. Biol.* 8: 3345–3356 (1988); Kypta, et al. *Cell* 62: 481–492 (1990)). These signaling molecules are thought to mediate at least in part the mitogenic effects of TKRs (Ullrich, et al. supra; Aaronson, supra).

However, the Epidermal growth factor (EGF) receptor (EGFR) does not appear to efficiently interact with known second messenger systems (Fazioli, et al. *Mol. Cell. Biol.* 11: 2040–2048 (1991); Segatto, et al. *Mol. Cell. Biol.* 11: 3191–3202 (1991)). Thus, there is a need to ascertain the mechanism by which the EGFR functions in mitogenesis, and a particular need to identify and characterize the substrate (if any) of the EGFR.

Errors which occur in the mitogenic signaling pathway, such as alterations in one or more elements of that pathway, are implicated in malignant transformation and cancer. It is believed that in at least some malignancies, interference with such abnormal mitogenic signal transduction could cause the cells to revert to normal phenotype.

In addition, reagents useful in identifying molecular components of the mitogenic signaling pathway find utility as tumor markers for therapeutic, diagnostic, and prognostic purposes. Furthermore, identification of how such components differ from normal components in malignant tissue would be of significant value in understanding and treating such malignancies. Alterations of the EGFR mitogenic signal transduction have been described in several human tumors. Accordingly, substrates of EGFR are of particular interest.

Finally, there is a need for reagents for determining the tyrosine kinase activity of particular samples of biological origin.

It is therefore an object of the present invention to provide reagents and methods useful in identifying components of the mitogenic signal transduction pathway, for determining tyrosine kinase activity of samples, and for determining how particular components of the pathway in abnormal tissue differ from normal components. In particular, it is an object of the invention to provide such reagents and methods that relate to the substrate of the EGFR.

SUMMARY OF THE INVENTION

A method is disclosed which allows direct cloning of intracellular substrates for tyrosine kinase receptors (TKRs). By applying this technique to the study of the epidermal growth factor receptor (EGFR) signaling pathway, a cDNA which predicts an approximately 92 kDa protein designated eps8, bearing the characteristic signatures of TKR substrates including SH2 and SH3 domains, has been isolated. Eps8 also contains a putative nuclear targeting sequence. Antibodies specific to the eps8 gene product recognize two proteins of 97 kDa and 68 kDa which are closely related as demonstrated by V8 proteolytic mapping. The product of the eps8 gene associates with and is phosphorylated on tyrosine by the EGFR. Several other TKRs are also able to phosphorylate p97eps8 on tyrosine residues. Thus, the eps8 gene product represents a novel substrate for TKRs. Adoptive expression of the eps8 cDNA in fibroblastic or hematopoietic target cells expressing the EGFR resulted in increased mitogenic response to EGF implicating the eps8 gene product in the transduction of mitogenic signals.

Thus, one aspect of the present invention is isolated or enriched polynucleotide operably encoding an eps8 substrate of the epidermal growth factor receptor, preferably mammalian eps8, and more preferably human eps8. This human sequence can include polynucleotide encoding the amino acid sequence of SEQ ID NO:2, and can include the DNA sequence SEQ ID NO:1. Alternatively, the polynucleotide sequence can be an mRNA transcript of SEQ ID NO:1. Also included within the scope of the invention is a polynucleotide sequence which includes the protein-encoding domain of SEQ ID NO:3. Moreover, the invention includes an antisense mRNA sequence to the eps8 gene, preferably including at least 15 nucleotides.

The invention further comprises isolated eps8, preferably mammalian eps8, and more preferably human eps8. The human eps8 advantageously includes the amino acid sequence of SEQ ID NO:2. The invention further includes mouse eps8, having the amino acid sequence of SEQ ID NO:4. The concentration of the isolated or purified eps8 is preferably at least 1 μg/ml.

Another aspect of the invention is isolated antibody to eps8, including both monoclonal and polyclonal antibody.

Further, the invention includes a method for enhancing mitogenic response of cells to epidermal growth factor, comprising the step of administering to the cells an effective mitogenic-response enhancing amount of eps8.

Another aspect of the present invention is a method for determining tyrosine kinase activity in a biological sample, comprising the steps of combining eps8 with the sample, and measuring tyrosine phosphorylation of the eps8 by tyrosine kinase in the sample.

Finally, the invention includes a method for determining eps8 in a sample, comprising the steps of contacting the sample with antibody to eps8, such that an immunological complex forms between eps38 and the antibody, and detecting the formation of the immunological complex.

DETAILED DESCRIPTION OF THE INVENTION

A. Overview

In the case of the Epidermal growth factor (EGF) receptor (EGFR) expressed in murine fibroblasts, two lines of evidence indicate that this receptor is not very efficient at coupling with known second messenger systems. There is a low stoichiometry of tyrosine phosphorylation (~1% of the total pools), of PLC-γ, and GAP weak induction of PIP2 breakdown, and no phosphorylation/activation of raf or activation of PtdIns-3K by EGFR, even when overexpressed at levels of approximately $2 \times 10^6$ receptors/cell (Fazioli, et al. *Mol. Cell Biol.* 11: 2040–2048 (1991)). In addition, a mitogenesis-incompetent mutant of the EGFR (EGFR Δ660–667 Segatto, et al., *Mol. Cell Biol.* 11:3191–3202 (1991)) did not show any decreased ability to phosphorylate PLC-γ or GAP, or to induce PIP2 breakdown as compared to the wild type EGFR (Segatto, et al., supra). This strongly indicates the existence of alternative effector pathways for mitogenic signal transduction by EGFR.

Characterization of EGFR-activated pathways requires the identification of novel proteins that are tyrosine phosphorylated following stimulation of this receptor kinase. The present invention utilized a novel approach to the cloning of cDNAs coding for EGFR substrates, as disclosed in Fazioli, et al. *J. Biol. Chem.* 267: 5155–5157 (1992), which is hereby incorporated by reference. The approach relies on batch purification of the entire set of proteins that are phosphorylated on tyrosine following EGFR activation and generation of antisera directed against the entire pool of purified proteins. These sera can be used to immunologically characterize various substrates or for expression screening of cDNA libraries.

The present invention includes the discovery of a novel EGFR substrate isolated by this approach, which is called eps8, together with complete cDNA and predicted protein sequences for the murine eps8 (SEQ ID NOS:3 and 4, respectively) and partial cDNA and predicted protein sequences for the human eps8 (SEQ ID NOS:1 and 2, respectively). The protein sequences are referred to as "predicted" sequences simply because they were determined from the nucleotide sequence, rather than from analysis of purified natural protein.

In addition, the present invention provides methodology for isolating the complete human cDNA and protein sequences, as well as those of other species; antibodies which recognize the protein encoded by the cDNA; expression vectors for producing eps8 in prokaryotic or eucaryotic cells; cell lines overexpressing eps8 ; and assays using the antibodies, cDNA sequences, and proteins.

The eps8 proteins, polynucleotide sequences, constructs, vectors, clones, and other materials comprising the present invention can advantageously be in enriched or isolated form. As used herein, "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated.

The term "isolated" requires that the material be removed from its original environment (e.g., the natural environment if it is naturally occurring). For example, a naturally-occurring polynucleotide present in a living animal is not isolated, but the same polynucleotide, separated from some or all of the coexisting materials in the natural system, is isolated.

It is also advantageous that the protein or the sequences be in purified form. The term "purified" does not require absolute purity; rather, it is intended as a relative definition, with reference to the purity of the material in its natural state. Purification of natural material to at least one order of magnitude, preferably two or three orders, and more preferably four or five orders of magnitude is expressly contemplated.

B. Identification of Murine cDNA Encoding eps8

Antibodies to phosphotyrosine were used to isolate proteins that are tyrosine-phosphorylated upon EGF stimulation of NIH-3T3 murine fibroblasts overexpressing the EGFR (NIH-EGFR cells), as discussed in Example 1. A strategy was developed that allowed direct cloning of the cDNAs encoding several of these proteins. Briefly, two polyclonal sera were generated using the entire purified pool of phosphotyrosine (pTyr)-containing proteins as an immunogen (Fazioli, et al. *J. Biol. Chem.* supra). These antibodies were used to screen cDNA clones, as reported in greater detail in Examples 1 and 2.

A novel cDNA isolated by this method was sequenced as described in Example 3, and the encoded protein was designated eps8. The amino acid sequence (SEQ ID NO:4) predicts a protein bearing the characteristic hallmarks of TKR substrates. Antibodies generated to the cDNA protein product in accordance with Example 4 recognized a 97 kDa protein and a less abundant 68 kDa protein which were phosphorylated on tyrosine residues following treatment of intact cells with EGF.

C. Features and Properties of eps8 Protein

The amino acid sequence deduced from the single eps8 ORF (SEQ ID NO:4) predicted an 821 amino acid protein with a calculated molecular weight of 91738 daltons.

One relevant feature of the predicted sequence of the eps8 gene product is the presence of unique SH2 and SH3 signatures. The SH2 domain was first identified as a non-catalytic motif of sequence homology between cytoplasmic tyrosine kinases, and was subsequently recognized in other proteins, including molecules involved in mitogenic signaling such as PLC-γ and GAP (Koch, et al. *Science* 252: 668–674 (1991)). The SH2 domain is thought to mediate the binding of substrates to receptors by recognizing tyrosine-phosphorylated motifs (Anderson, et al. *Science* 250: 979–981 (1990), Matsuda, et al. *Science* 248:1537–1539 (1990), Mayer, et al. *Proc. Natl. Acad. Sci. USA* 87: 2638–2642 (1990), Moran, et al. *Proc. Natl. Acad. Sci. USA* 87: 8622–8626 (1990), Margolis, et al. *EMBO J.* 9: 4375–4380 (1991)). Variations in the number position and primary sequence of the SH2 domains also suggest that they may serve different recognition functions. Indeed, there is evidence that known kinase substrates such as GAP, p85, and PLC-γ interact with different regions of the platelet-derived growth factor receptor and do not compete for their respective binding sites (Morrison, et al. *Mol. Cell. Biol.* 10: 2359–2366 (1990), Escobedo, et al. *Mol. Cell. Biol.* 11: 1125–1132 (1991)). In this regard, it is of note that the SH2 domain of the eps8 gene product, although readily recognizable, displayed significant variations in the primary sequence when compared to other analogous domains. The eps8 SH2 domain is also unique in its relative position within the molecule, being located at the very amino-terminus.

The SH2 domain of the eps8 gene product extended between position 2 and 120 of the predicted protein sequence and displayed the highest level of identity with the analogous domains of c-src and v-crk. In the conserved regions of the SH2 consensus (defined according to Koch, et al. supra), eps8 displayed 40% and 32% identity with c-src and v-crk respectively, whereas the latter two proteins showed 45% identity between themselves. Notably, eps8 lacked the initial WY/F motif (which is well conserved among SH2 domains), but retained the 3 conserved basic residues that are thought to be involved in SH2/phosphotyrosine interactions (Koch, et al. supra).

The product of the eps8 gene also contained an SH3 domain. Understanding of the function of SH3 regions is preliminary. The sequence is contained in several of the proteins bearing an SH2 domain (Koch, et al. supra) but is also observed in a number of other species. These include cytoskeletal proteins (Jung, et al. *Proc. Natl. Acad. Sci. USA* 84: 6720–6724 (1987), Wasenius, et al. *J. Cell Biol.* 108: 79–93 (1989), and Drubin, et al. *Nature* 343: 288–290 (1990)); putative transcription factors like HS-1 (Kitamura, et al. *Nucl. Acids Res.* 17: 9367–9379 (1989)); yeast proteins involved in control of proliferation (Broek, et al. *Cell* 48: 789–799 (1987), and Hughes, et al. *Nature* 344: 355–357 (1990)) and cell fusion (Trueheart, et al. *Mol. Cell. Biol.* 7: 2316–2328 (1987)); and the neutrophil oxidase factor 67-kD (Leto, et al. *Science* 248: 727–730 (1990)). In addition, mutations in the SH3 domain of v-src attenuated its ability to depolymerize acting filaments (reviewed in Koch, et al. supra). Thus, this domain may direct protein-protein interactions in the cytoskeleton.

The eps8 gene product did not display sequence features that would readily identify an enzymatic activity. In this regard it may be classified with proteins like v-crk or nck which are also apparently devoid of intrinsic activity (Koch, et al. supra). These proteins have been proposed to serve as molecular adapters, juxtaposing by virtue of their SH2 domains a TKR to other effector molecules (reviewed in Koch, et al. supra). A similar function could be reasonably postulated for the eps8 gene product. However, at variance with v-crk and nck, the eps8 gene product presents two long stretches of sequence of about 400 and 250 amino acids with no detectable homology to other proteins. Thus, it may also contain determinants responsible for some intrinsic, yet-to-be-discovered function. A physiological role of eps8 is suggested by the observation that it contains a putative nuclear targeting sequence.

In addition, coimmunoprecipitation experiments demonstrated physical association between the eps8 gene products(s) and the EGFR. Thus, the eps8 protein represents an authentic substrate for the EGFR kinase.

No other region of extensive sequence homology with proteins present in databanks was demonstrable. Notably, a stretch rich in basic amino acids extending from position 299 to 309 of SEQ ID NO:4 contained a putative nuclear targeting sequence RKKSK (Gomez-Marquez, et al. *FEBS Lett.* 226: 217–219 (1988)). Structural analysis of the predicted eps8 product revealed a high turn propensity due to the elevated proline content of the protein (7.9%). An hydropathy plot revealed a rather hydrophilic profile consistent with the relatively high content in charged amino acids (25.5%) and no long hydrophobic stretches that could encode a transmembrane domain or a signal peptide.

D. Obtaining Partial and Complete Human cDNA for eps8

The present invention includes partial and complete human cDNA sequences and human genomic DNA sequences for eps8. A partial cDNA sequence for human eps8 is set forth as SEQ ID NO:1, and the corresponding predicted peptide sequence is set forth as SEQ ID NO:2. The partial sequence of SEQ ID NO:1 was obtained by PCR amplification from a human cDNA library using short sequences of the mouse eps8 cDNA (SEQ ID NO:3) as primers. This procedure is explained in more detail in Example 5.

The partial human cDNA sequence of SEQ ID NO:1 can be used as a probe to identify a cDNA clone corresponding to a full-length transcript. The full length sequence can then be routinely determined by sequencing of that clone. The partial or full-length cDNA clone can also be used as a probe to identify a genomic clone or clones that contain the complete gene including regulatory and promoter regions, exons, and introns. Finally, an expression product of the partial sequence can be used for expression screening of a cDNA library, using the techniques set forth in Example 4 to generate polyclonal antibody against human eps8, and then screening clones to identify candidates as set forth in Example 2, followed by sequencing as set forth in Example 3.

One general procedure for obtaining a complete DNA sequence corresponding to the partial human sequence disclosed herein is as follows:

1. Label a partial sequence and use it as a probe to screen a lambda phage human cDNA library or a plasmid cDNA library.
2. Identify colonies containing clones related to the probe cDNA and purify them by known purification methods.
3. Nucleotide sequence the ends of the newly purified clones to identify full length sequences.
4. Perform complete sequencing of full length clones by Exonuclease III digestion or primer walking. Northern blots of the mRNA from various tissues using at least part of the clone as a probe can optionally be performed to check the size of the mRNA against that of the purported full length cDNA.

More particularly, all or part of the DNA sequence of SEQ ID NO:1 may be used as a probe to identify a cDNA clone containing the full length cDNA sequence. The partial sequence of SEQ ID NO:1, or portions thereof, can be nick-translated or end-labelled with $^{32}P$ using polynucleotide kinase and labelling methods known to those with skill in the art (*Basic Methods in Molecular Biology*, L. G. Davis, M. D. Dibner, and J. F. Battey, ed., Elsevier Press, N.Y. 1986). A lambda library can be directly screened with the labelled cDNA probe, or the library can be converted en masse to pBluescript (Stratagene, LaJolla, Calif.) to facilitate bacterial colony screening. Both methods are well know in the art.

Briefly, filters with bacterial colonies containing the library in pBluescript or bacterial lawns containing lambda plaques are denatured and the DNA is fixed to the filters. The filters are hybridized with the labelled probe using hybridization conditions described by Davis, et al. The partial sequence, cloned into lambda or pBluescript, can be used as a positive control to assess background binding and to adjust the hybridization and washing stringencies necessary for accurate clone identification. The resulting autoradiograms are compared to duplicate plates of colonies or plaques; each exposed spot corresponds to a positive colony or plaque. The colonies or plaques are selected, expanded, and the DNA is isolated from the colonies for further analysis and sequencing.

Positive cDNA clones in phage lambda may be analyzed to determine the amount of additional sequence they contain using PCR with one primer from the partial sequence (SEQ ID NO:1) and the other primer from the vector. Clones with a larger vector-insert PCR product than the original clone are analyzed by restriction digestion and DNA sequencing to determine whether they contain an insert of the same size or similar as the mRNA size on a Northern blot.

Once one or more overlapping cDNA clones are identified, the complete sequence of the clones can be determined. The preferred method is to use exonuclease III digestion (McCombie, W. R., Kirkness, E., Fleming, J. T., Kerlavage, A. R. Iovannisci, D. M., and Martin-Gallardom R., Methods: 3: 33– 40, (1991)). A series of deletion clones is generated, each of which is sequenced. The resulting overlapping sequences are assembled into a single contiguous sequence of high redundancy (usually three to five overlapping sequences at each nucleotide position), resulting in a highly accurate final sequence.

A similar screening and clone selection approach can be applied to obtaining cosmid or lambda clones from a genomic DNA library that contains the complete gene from which the partial sequence was derived (Kirkness, E. F., Kusiak, J. W., Menninger, J., Gocayne, J. D., Ward, D. C., and Venter, J. C. *Genomics* 10: 985–995 (1991)). Although the process is much more laborious, these genomic clones can also be sequenced in their entirety. A shotgun approach is preferred to sequencing clones with inserts longer than 10 kb (genomic cosmid and lambda clones). In shotgun sequencing, the clone is randomly broken into many small pieces, each of which is partially sequenced. The sequence fragments are then aligned to produce the final contiguous sequence with high redundancy. An intermediate approach is to sequence just the promoter region and the intron-exon boundaries and to estimate the size of the introns by restriction endonuclease digestion.

E. Expression of eps8 Gene

With the sequence of the eps8 gene in hand, it is routine to express that gene in a recombinant organism to obtain significant amounts of eps8. One example of a suitable expression vector and host is set forth in Example 4. Alternatively, the DNA encoding eps8 can be inserted into other conventional host organisms and expressed. The organism can be a bacterium, yeast, cell line, or multicellular plant or animal. The literature is replete with examples of suitable host organisms and expression techniques. For example, naked polynucleotide (DNA or mRNA) can be injected directly into muscle tissue of mammals, where it is expressed. This methodology can be used to deliver the polynucleotide and, therefore, the resulting polypeptide translation product to the animal, or to generate an immune response against a foreign polypeptide (Wolff, et al. *Science* 247:1465 (1990); Felgner, et al. *Nature* 349:351 (1991)). Alternatively, the coding sequence, together with appropriate regulatory regions (i.e., a construct), can be inserted into a vector, which is then used to transfect a cell. The cell (which may or may not be part of a larger organism) then expresses the polypeptide.

F. In vivo Transcription of eps8

In order to assess the expression of mRNA encoded by the eps8 gene, we performed Northern blot analysis of poly(A)+ RNA extracted from NIH-3T3 cells using the pl 8 insert as a probe. Two major bands of ~3.8 and ~4.7 kb were detected. The size of the smaller band is in agreement with that of the longest eps8 cDNA clone. The nature of the 4.7 kb band is not resolved. It is unlikely that the band represents a related species since hybridization was performed under conditions of high stringency. Thus, it most likely represents a partially processed precursor or an alternatively spliced form.

G. Assays for Detecting eps8

Antibodies generated against the polypeptide corresponding to a sequence of the present invention can be obtained by direct injection of the naked polynucleotide into an animal (Wolff, supra) or by administering the polypeptide to an animal, as explained in Example 4. The antibody so obtained will then bind the polypeptide itself. In this manner, even a sequence encoding only a fragment of eps8 can be used to generate antibodies binding the whole native polypeptide.

Antibodies generated in accordance with Example 4 can be used in standard immunoassay formats to detect the presence and/or amount of eps8 in a sample. Such assays can comprise competitive or noncompetitive assays. Radioimmunoassays, ELISAs, Western Blot assays, immunohistochemical assays, immunochromatographic assays, and other conventional assays are expressly contemplated. Furthermore, polyclonal antibodies against human or other eps8 can be readily generated using the techniques of Example 4, and monoclonal antibodies to any form of eps8 can be generated using well-known methods. All of these antibodies can be used in assays of the present invention, and the assays and the antibodies form a part of this invention.

H. Detection of TKR Activity

In many instances, it is important to know the tyrosine kinase activity of a sample. The present invention provides a ready method by which such activity can be determined. As discussed in more detail herein, eps8 is tyrosine phosphorylated by the EGFR as well as by other tyrosine kinase receptors. This ability of TKRs to phosphorylate eps8 is exploited to measure the presence of TKRs in a sample.

Briefly, one method for such measurement is to contact a sample with eps8, add radiolabeled γ-ATP to the sample and then measure the extent to which the radiolabel is incorporated into the eps8. Anti-eps8 antibodies may be used in the final step of the assay to capture eps8 for measurement of phosphorylation. Such assays are disclosed in more detail in Examples 9 and 10.

Alternatively, the ability of TKRs to bind eps8 can be utilized to measure the presence of TKRs in a sample. Labeled eps8 (e.g., radiolabeled, enzyme labeled, colorimetrically labeled) can be added to a sample where it binds EGFR or other TKR in the sample. The biological sample to be analyzed should be obtained, for this purpose, in the presence of low concentration of non-ionic detergents, such as 1% NP-40 or 1% Triton-X-100, to allow formation of the eps8-TKR complex and prevent its dissociation. These conditions are advantageous for two reasons: first, most, if not all, of the TKRs (and other tyrosine kinases of non-receptorial type) can be completely solubilized from biological materials under these conditions. Second, the eps8/EGFR complex is stable under these conditions. The resulting complex is then isolated and measured, using conventional chromatographic or immunological techniques. For example, the esp8/TKR complex can be recovered with an anti-eps8 antibody, and the presence of TKRs (or other tyrosine kinases) can be detected with specific antibodies against individual TKRs or with an anti-phosphotyrosine antibody. Several kind of assays can be used for this purpose, including, but not exclusively, immunoblot, ELISA, and radioimmunoassays.

I. Detection of Altered Mitogenic Signal Transduction

The eps8 of the present invention is also valuable in detection of altered mitogenic signal transduction. Such altered signal transduction can be ascertained by measurement of eps8 levels in vivo or in vitro using the immunoassays discussed above. Alternatively, altered forms of eps8 can be detected by using at least a portion of the DNA encoding eps8 as a probe to isolate the DNA encoding a possibly altered form of eps8. Techniques of the type disclosed in Examples 2 and 3, or other conventional techniques, can then be used to sequence the isolated DNA. By comparing this sequence to the known sequence, alterations can be detected.

If an altered eps8 sequence or abnormal labels of eps8 are detected in malignant tissue, antisense therapy can be utilized in accordance with Example 11 to halt translation of the protein and, thus, to interfere with mitogenesis.

J. Increasing the Mitogenic Response of Cells

The mitogenic response of cells can be enhanced by delivering eps8 to the cell in amounts greater than the natural amounts. Although the optimum dosage for any particular cell type can be empirically determined in a relatively straightforward manner, it is apparent that any increased dosage will have a mitogenesis-enhancing effect.

Particular aspects of the invention may be more readily understood by reference to the following examples, which are intended to exemplify the invention, without limiting its scope to the particular exemplified embodiments.

EXAMPLE 1

Generation of Polyclonal Antibody Against EGFR Substrates

Immunoaffinity chromatography techniques were used to isolate proteins which were tyrosine phosphorylated by EGFR, as described by Fazioli, et al. *J. Biol. Chem.* 267:5155–5161 (1992). Briefly, genetically engineered NIH-3T3 cells which overexpress EGFR (NIH-EGFR) (Fazioli, et al. *Mol. Cell Biol.* 11:2040–2048 (1991)) were maintained in DMEM (Gibco, Gaithersburg, Md.) supplemented with 10% calf serum (Gibco, supra). Subconfluent cell monolayers were treated with EGF (Upstate Biotechnology, Inc. (UBI), Lake Placid, N.Y.), and lysed. EGFR was removed from the lysate using an anti-EGFR column prepared by linking anti-EGFR monoclonal antibody (Ab1, Oncogene Science, Uniondale, N.Y.) to agarose beads. The lysate was then contacted with an anti-phosphotyrosine (anti-pTyr, Oncogene Science, supra) column; the column was washed; and the bound protein was then eluted. Fractions were collected and were used to immunize two New Zealand white rabbits, yielding two polyclonal immune sera, designated 450 and 451.

EXAMPLE 2

Identification of eps8 cDNA Clone

A pool of sera 450 and 451 from Example 1 was used to screen a commercial (Clontech, Palo Alto, Calif.) λgt11 library from NIH-3T3 cells. Recombinant plaques ($10^6$) were initially screened with a 1:200 dilution of each antibody in TTBS (0.05% Tween 20 mMTris-HCl [pH 7.5] 150 mM NaCl) containing 1% BSA. Detection was carried out with a goat anti-rabbit Ab conjugated to alkaline phosphates by utilizing a commercial kit (Picoblue, Stratagene, La Jolla, Calif.) according to the manufacturer's specification. Analysis yielded several positive plaques; one of these clones (pl 8) contained an insert of ~1.6 kbp which was completely sequenced and showed no corresponding to sequences present in the Genbank or EMBL data banks. The pl 8 insert was subcloned in the EcoRI site of pBluescript (Stratagene, supra).

The sequence of pl 8 predicted an ORF which started in the expected frame with the β-galactosidase portion of λgt11 and terminated at position 1081–1083 with a stop codon. The pl 8 cDNA, however, displayed no initiation codon. It was concluded that pl 8 represented a partial cDNA encoding a novel protein, now designated eps8 (for EGFR-pathway substrate #8).

EXAMPLE 3

Isolation and Sequencing of eps8 cDNA

Full length cDNA for eps8 was obtained by screening a mouse keratinocyte cDNA library (Miki, et al. *Science* 251: 72–75 (1991)) using the pl 8 insert from Example 2 as a probe according to standard procedures (Sambrook, et al. *Molecular Biology: A Laboratory Manual* (Cold Spring Harbor Laboratory press 1989)). Several recombinant phages were isolated, the longest containing an insert of ~3.6 kbp. DNA sequence was performed on this sequence by the dideoxy-termination method on both strands of the cDNA, using a commercial kit (Sequenase, United States Biochemical, Cleveland, Ohio). The resulting DNA sequence is identified herein as SEQ ID NO:3. The sequence contains a stop codon at position 2708–2710 followed by a 3' untranslated sequence containing a canonical polyadenylation site (AATAAA) starting at position 3035. Three putative ATG initiation codons were identified at positions 246–248, 258–260, and 336–338, respectively. Only the first ATG conformed to Kozak's rules for translational initiation (Kozak, M. *J. Cell Biol.* 108: 229–241 (1989)) and was preceded by an in-frame stop codon at position 222–224; thus it is believed to represent the translation initiation codon.

EXAMPLE 4

Preparation of Anti-eps8 Antibody and Expression of eps8 gene Product

Polyclonal antibodies specific for the eps8 gene product were generated against a recombinant glutathione S-transferase fusion protein. To this end the open reading frame (ORF) of pl 8 (between positions 246 and 2708 of SEQ ID NO:3) was modified by adding an inframe Bam HI restriction site to its 5' end using recombinant PCR (Higuchi, R. PCR Protocols: *A Guide to Methods and Applications*, eds. Innis M. A. Gelfand D. H., Sninsky J. J. & White T. J. (Academic press San Diego, Calif.) pp 177–183 (1990)). The BaHI I- EcoR I fragment containing the entire ORF (pl 8) was cloned between the homologous sites of the pGEX expression plasmid (Pharmacia, Piscataway, N.J.). The recombinant fusion protein was expressed following the manufacturer's specifications and used to immunize New Zealand rabbits. In addition, an anti-eps8 specific peptide serum was generated against the synthetic peptide Y corresponding to amino acid positions 784–803 of SEQ ID NO:4, the predicted eps8 protein. The peptide was conjugated to a macromolecular carrier (key limpet hemocyanin) and used to immunize New Zealand rabbits. A commercially available anti-phosphotyrosine (anti-pTyr) monoclonal antibody (Upstate Biotechnology, Lake Placid, N.Y.) was also used. Specificity of detection for anti-pTyr was controlled as described previously (Fazioli, et al. *Mol. Call Biol.* supra and Fazioli, et al. *J. Biol. Chem.* supra, which are both incorporated by this reference).

This antibody specifically recognized a major species of Mr 97 kDa (p97eps8) and a minor component of 68 kDa (p68eps8) in NIH-EGFR cells. The size of the major component was consistent with the predicted molecular weights of the eps8 gene product. Both p97eps8 and p68eps8 underwent a mobility shift upon in vivo EGF treatment, suggesting EGF-induced post-translation modification, possibly tyrosine phosphorylation. Indeed, sequential immunoprecipitation and immunoblotting with anti-pTyr and anti-eps8 antibodies indicated that p97eps8 is phosphorylated in vivo on tyrosine following EGFR activation.

Anti-pTyr recovery of the eps8 product might be due to direct recognition of phosphotyrosil residues or to association with other pTyr-containing proteins. To distinguish between these possibilities immunoprecipitation experiments with anti-eps8 were performed, followed by immunoblot with anti-pTyr. It was found that p97eps8 was readily detectable under these conditions in cell lysates obtained from NIH-EGFR cells triggered with EGF. Under these conditions, p68eps8 exhibited detectable pTyr content as well. In addition, EGF-induced tyrosine phosphorylation of both eps38 proteins was detected by phosphoamino acid analysis of $^{32}$P-labeled p97eps8 and p68eps8.

Anti-pTyr immunoblotting also revealed a 170 kDa protein which was specifically immunoprecipitated by the anti-eps8 antibody following EGF treatment of intact cells. Its size was consistent with the possibility that it represented the EGFR co-immunoprecipitated with one of the eps8 products. To test this possibility, cell lysates obtained under mild condition to preserve protein-protein interactions were immunoprecipitated with the anti-eps8 serumand immunoblotted with a specific anti-EGFRserum. Under these conditions, the EGFR was readily detectable following EGF treatment of intact cells, indicating physical association between the receptor and the eps8 gene product(s).

To further investigate the nature of p97eps8 and p68eps8, we performed limited V8-protease digestions by the Cleveland method (Cleveland, et al. *J. Biol. Chem.* 252: 1102–1106 (1977)). A number of common proteolytic fragments were detectable in p97eps8 and p68eps8, indicating that the two proteins are highly related.

EXAMPLE 5

Derivation of Partial Human eps8 Sequences

The partial human eps8 sequence of SEQ ID NO:1 was obtained by the polymerase chain reaction (PCR) method using two oligonucleotides from the mouse eps8 cDNA sequence as primers to amplify the human cDNA fragment from a human cDNA library. The library used was from A101D cells (human melanoma cells, Giard, et al. *J. Nat'l Cancer Institute* 51:1417–1423 (1973)), although other readily-available libraries could be used. The library was prepared using the method of Miki, et al., *Science* 251:72–75 (1991). The two oligonucleotide PcR primers were:

1) 5' CGAGCTCGAGAGATCAGCTGACACTCCTTCT (SEQ ID NO:5)

2) 5' CGATATCGATTCTCTTGTAACTCGGAGCTTC (SEQ ID NO:6)

corresponding to positions 2088–2107 and 2608–2628 of the mouse eps8 cDNA sequence (SEQ ID NO:3), respectively. A typical PCR contained 100 ng of cDNA library DNA, 5 units of Taq DNA polymerase (Boehringer Mannheim, Indianapolis, Ind.), 1 μM of each oligonucleotide primer, 200 μM dNTPs, 10 mM Tris-HCl (pH 8.3), 1.5 mM MgCl$_2$, 50 mM KCl, 0.1 mg/ml gelatin. Reactions were carried out for 35 cycles of 1.5 min at 94° C., 5 min at 50° C., and 2 min at 72° C. Reactions were then terminated with an additional 10 min at 72° C. The PCR products were purified by chroma spin+TE –400 column (Clontech, Palo Alto, Calif.), subcloned into pBluescript II KS vector (Stratagene, La Jolla, Calif.), and sequenced by the dideoxy-termination methods on both strands using the Sequenase DNA sequencing kit (USB, Cleveland, Ohio).

EXAMPLE 6

Derivation of Complete Human eps8 Sequences

Using the partial sequence of SEQ ID NO:1 as a probe, a cDNA library generated from A101D cells (or other human library) is screened using the techniques described in Example 3. Several recombinant phages are isolated, and are compared to the known mouse sequence, SEQ ID NO:3. DNA sequencing is performed on the most promising cDNA by the dideoxy-termination method, as explained in Example 3.

EXAMPLE 7

Isolation of eps8 Sequences from other Organisms

Two potentially complementary strategies are used to isolate and clone the eps8 gene in other species. The first one is essentially the same as the one used to obtain the human partial cDNA for eps8. Briefly, two oligonucleotides from the mouse or the human eps8 sequence can be used to amplify, by the PeR method, fragments of eps8 cDNA from other species. The oligonucleotides can be designed from regions of high nucleotide identity between the human and mouse sequence, in a way to increase the probability of obtaining an efficient matching of the primers with the eps8 sequences of other species. The template for the PCR reaction can be a cDNA library from cells of another species or a cDNA obtained by reverse transcriptase (in the so called reverse transcriptase/PCR) directly from the mRNA of another species.

A second approach relies on classical low stringency hybridization of nucleic acids. In this case a probe representing the eps8 cDNA from human or mouse is hybridized, under relaxed conditions of stringency, against libraries (cDNA or genomic) prepared from cells of other species. Relaxed stringency is obtained by modifying the temperature and the ionic strength of the hybridization buffer, in a manner designed to allow stable formation of hybrids which are not 100% matching (as expected in inter-species hybridization). The positives are then analyzed as described above (see Example 6). A complete review on low stringency hybridization is to be found in Kraus, et al. Methods in *Enzymology* 200: 546–556 (1991), which is hereby incorporated by reference.

EXAMPLE 8

Quantitative Immunoassay for esp8

It is often desirable to determine the quantity of eps8 in a sample. This can be particularly useful in clinical research, as well as in detecting abnormalities in mitogenic signal transduction in malignant tissue. In addition, in many human tumors, tumor markers are released in the blood stream at levels which correlate with the size of the tumor and its clinical stage. Determination of the levels of a marker (such as eps8) in biological fluids can be advantageous in aiding the diagnostic procedures and in monitoring the effectiveness of therapy.

In one exemplary technique, anti-eps8 antibody from Example 4 is immobilized to an agarose column, as explained in Example 1. Sample is then directed through the column where eps8 in the sample is bound by the immobilized antibody. Next, a known quantity of radiolabeled anti-eps8 antibody is directed through the column. The quantity of labeled antibody which is not retained on the column is measured, and bears an relationship to the quantity of eps8 in the sample.

Another exemplary technique is liquid phase radioimmunoassay. First, a standard measurement is made. Specifically, a small, known amount of purified eps8, radiolabeled in a conventional manner, is challenged against a known amount of anti-eps38 antibody. The resulting immunocomplex is recovered by centrifugation, and the radioactivity of the centrifugate is determined. This value is used as a standard against which later measurements are compared.

Next, a sample, containing unknown amounts of eps8, is challenged against the same known amount (used in making the standard measurement) of anti-eps8 antibody. Then, the same amount of labeled eps8 used in making the standard measurement is added to the reaction mixture, followed by centrifugation and measurement of radioactivity as explained above. The decrease in the immunoprecipitated radioactivity (in comparison to the standard) is proportional to the amount of eps8 in the sample.

Of course, in addition to the foregoing exemplary methods, any of the well known conventional immunoassay methods may similarly be used.

EXAMPLE 9

Assay for Phosphorylation of eps8 by TKRs

A biological sample is assayed for TKR activity by combining the sample with known quantities of eps8 and $^{32}$P-labeled γ-ATP. The sample is then contacted with anti-eps8 from Example 4 immobilized on a column; the column is washed; and the bound eps8 is eluted with 0.1M glycine, pH 2.5. The eluant is then subjected to fractionation to separate the resulting radiolabeled eps8 from the free radioactivity in the sample using any conventional technique, such as precipitation in 5–10% trichloroacetic acid. Following fractionation, the amount of radioactivity incorporated into the eps8 is counted to measure TKR activity of the sample.

EXAMPLE 10

Alternative Assay for TKR Activity 100 ng of eps8 is added to 1 ml buffered cell lysate suspected of having tyrosine kinase activity, together with 30 μC $^3$P-γATP. Following incubation, the mixture is heated to 100° C. in a solution containing sodium lauryl sulfate (SDS) and β-mercaptoethanol. Aliquots are electrophoresed on 10–15% gradient SDS polyacrylamide gels and exposed to X-Omat X-ray film to identify radioactive eps8. Cell lysate from eps8-transfected cells incubated in the presence of radiolabeled amino acids is used to confirm the location on the gel of the phosphorylated eps8.

EXAMPLE 11

Preparation and Use of Antisense Oligonucleotides

Antisense RNA molecules are known to be useful for regulating translation within the cell. Antisense RNA molecules can be produced from the sequences of the present invention. These antisense molecules can be used as diagnostic probes to determine whether or not a particular gene is expressed in a cell. Similarly, the antisense molecules can be used as a therapeutic agent to regulate gene expression.

The antisense molecules are obtained from a nucleotide sequence by reversing the orientation of the coding region with regard to the promoter. Thus, the antisense RNA is complementary to the corresponding mRNA. For a review of antisense design see Green et al., *Ann. Rev Biochem.* 55:569–597 (1986), which is hereby incorporated by reference. The antisense sequences can contain modified sugar phosphate backbones to increase stability and make them less sensitive to RNase activity. Examples of the modifications are described by Rossi et al., *Pharmocol. Ther.* 50(2):245–254, (1991).

Antisense molecules are introduced into cells that express the eps8 gene. In a preferred application of this invention, the effectiveness of antisense inhibition on translation can be monitored using techniques that include but are not limited to antibody-mediated tests such as RIAs and ELISA, functional assays, or radiolabeling. The antisense molecule is introduced into the cells by diffusion or by transfection procedures known in the art. The molecules are introduced onto cell samples at a number of different concentrations, preferably between $1\times10^{-10}$M to $1\times10^{-4}$M. Once the minimum concentration that can adequately control translation is identified, the optimized dose is translated into a dosage suitable for use in vivo. For example, an inhibiting concentration in culture of $1\times10^{-7}$M translates into a dose of approximately 0.6 mg/kg bodyweight. Levels of oligonucleotide approaching 100 mg/kg bodyweight or higher may be possible after testing the toxicity of the oligonucleotide in laboratory animals.

The antisense can be introduced into the body as a bare or naked oligonucleotide, oligonucleotide encapsulated in lipid, oligonucleotide sequence encapsidated by viral protein, or as oligonucleotide contained in an expression vector such as those described in Example 3. The antisense oligonucleotide is preferably introduced into the vertebrate by injection. Alternatively, cells from the vertebrate are removed, treated with the antisense oligonucleotide, and reintroduced into the vertebrate. It is further contemplated that the antisense oligonucleotide sequence is incorporated into a ribozyme sequence to enable the antisense to bind and cleave its target. For technical applications of ribozyme and antisense oligonucleotides, see Rossi, et al. supra.

What is claimed is:

1. Isolated antibody to human eps8, said eps8 having amino acid sequence SEQ ID NO:2.

2. Isolated antibody to murine eps8, said eps8 having amino acid sequence SEQ ID NO:4.

3. Isolated antibody to eps8, said eps8 encoded by a polynucleotide that contains a protein-encoding domain, said polynucleotide hybridizes under high stringency conditions to DNA selected from the group consisting of:

(a) DNA encoding the amino acid sequence of SEQ ID NO:2;
(b) DNA encoding the amino acid sequence of SEQ ID NO:4;
(c) DNA sequence SEQ ID NO:1; and
(d) the protein-encoding domain of SEQ ID NO:3.

4. Monoclonal antibody to human eps8, said eps8 having amino acid sequence SEQ ID NO:2.

5. Monoclonal antibody to murine eps8, said eps8 having amino acid sequence SEQ ID NO:4.

6. Monoclonal antibody to eps8, said eps8 encoded by a polynucleotide that contains a protein-encoding domain, said polynuclestide hybridizes under high stringency conditions to DNA selected from the group consisting of:

(a) DNA encoding the amino acid sequence of SEQ ID NO:2;
(b) DNA encoding the amino acid sequence of SEQ ID NO:4;
(c) DNA sequence SEQ ID NO:1; and
(d) the protein-encoding domain of SEQ ID NO:3.

7. A method of determining eps8 in a sample, comprising the steps of:

contacting the sample with antibody of any of claims 1, 2, 3, 4, 5, or 6, such that an inmaunological complex forms; and detecting the formation of the immunological complex.

\* \* \* \* \*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 499 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..498

( x i ) SEQUENCE DESCRIPTION: SEQ ID NO:1:

```
GCT  CCA  TCA  CCT  CCT  CCA  ACA  CCA  GCT  CCT  GTT  CCT  GTT  CCC  CTT  CCC     48
Ala  Pro  Ser  Pro  Pro  Pro  Thr  Pro  Ala  Pro  Val  Pro  Val  Pro  Leu  Pro
 1              5                        10                       15

CCT  TCC  ACT  CCA  GCA  CCT  GTT  CCT  GTG  TCA  AAG  GTC  CCA  GCA  AAT  ATA     96
Pro  Ser  Thr  Pro  Ala  Pro  Val  Pro  Val  Ser  Lys  Val  Pro  Ala  Asn  Ile
             20                        25                       30

ACA  CGT  CAA  AAC  AGC  AGC  TCC  AGT  GAC  AGT  GGT  GGC  AGT  ATC  GTG  CGA    144
Thr  Arg  Gln  Asn  Ser  Ser  Ser  Ser  Asp  Ser  Gly  Gly  Ser  Ile  Val  Arg
        35                        40                       45

GAC  AGC  CAG  AGA  CAC  AAA  CAA  CTT  CCG  GTG  GAC  CGA  AGG  AAA  TCT  CAG    192
Asp  Ser  Gln  Arg  His  Lys  Gln  Leu  Pro  Val  Asp  Arg  Arg  Lys  Ser  Gln
    50                        55                       60

ATG  GAG  GAA  GTG  CAA  GAT  GAA  CTC  ATC  CAC  AGA  CTG  ACC  ATT  GGT  CGG    240
Met  Glu  Glu  Val  Gln  Asp  Glu  Leu  Ile  His  Arg  Leu  Thr  Ile  Gly  Arg
65                       70                       75                       80

AGT  GCC  GCT  CAG  AAG  AAA  TTC  CAT  GTG  CCA  CGG  CAG  AAC  GTG  CCA  GTT    288
Ser  Ala  Ala  Gln  Lys  Lys  Phe  His  Val  Pro  Arg  Gln  Asn  Val  Pro  Val
                    85                       90                       95

ATC  AAT  ATC  ACT  TAC  GAC  TCC  ACA  CCA  GAG  GAT  GTG  AAG  ACG  TGG  TTA    336
Ile  Asn  Ile  Thr  Tyr  Asp  Ser  Thr  Pro  Glu  Asp  Val  Lys  Thr  Trp  Leu
               100                      105                      110

CAG  TCA  AAG  GGA  TTC  AAC  CCT  GTG  ACT  GTC  AAT  AGT  CTT  GGA  GTA  TTA    384
Gln  Ser  Lys  Gly  Phe  Asn  Pro  Val  Thr  Val  Asn  Ser  Leu  Gly  Val  Leu
          115                      120                      125

AAT  GGT  GCA  CAA  CTT  TTC  TCT  CTC  AAT  AAG  GAT  GAA  CTG  AGG  ACA  GTC    432
Asn  Gly  Ala  Gln  Leu  Phe  Ser  Leu  Asn  Lys  Asp  Glu  Leu  Arg  Thr  Val
     130                      135                      140

TGC  CCT  GAA  GGG  GCG  AGA  GTC  TAT  AGC  CAA  ATC  ACT  GTA  CAA  AAA  GCT    480
Cys  Pro  Glu  Gly  Ala  Arg  Val  Tyr  Ser  Gln  Ile  Thr  Val  Gln  Lys  Ala
145                      150                      155                      160

GCA  TTA  GAG  GAG  AGC  AGT  G                                                    499
Ala  Leu  Glu  Glu  Ser  Ser
               165
```

( 2 ) INFORMATION FOR SEQ ID NO:2:

( i ) SEQUENCE CHARACTERISTICS:
        ( A ) LENGTH: 166 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Ala Pro Ser Pro Pro Pro Thr Pro Ala Pro Val Pro Val Pro Leu Pro
 1               5                  10                  15
Pro Ser Thr Pro Ala Pro Val Pro Val Ser Lys Val Pro Ala Asn Ile
                20                  25                  30
Thr Arg Gln Asn Ser Ser Ser Asp Ser Gly Gly Ser Ile Val Arg
            35                  40                  45
Asp Ser Gln Arg His Lys Gln Leu Pro Val Asp Arg Arg Lys Ser Gln
        50                  55                  60
Met Glu Glu Val Gln Asp Glu Leu Ile His Arg Leu Thr Ile Gly Arg
 65                  70                  75                  80
Ser Ala Ala Gln Lys Lys Phe His Val Pro Arg Gln Asn Val Pro Val
                85                  90                  95
Ile Asn Ile Thr Tyr Asp Ser Thr Pro Glu Asp Val Lys Thr Trp Leu
            100                 105                 110
Gln Ser Lys Gly Phe Asn Pro Val Thr Val Asn Ser Leu Gly Val Leu
            115                 120                 125
Asn Gly Ala Gln Leu Phe Ser Leu Asn Lys Asp Glu Leu Arg Thr Val
        130                 135                 140
Cys Pro Glu Gly Ala Arg Val Tyr Ser Gln Ile Thr Val Gln Lys Ala
145                 150                 155                 160
Ala Leu Glu Glu Ser Ser
                165
```

( 2 ) INFORMATION FOR SEQ ID NO:3:

( i ) SEQUENCE CHARACTERISTICS:
        ( A ) LENGTH: 3245 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 246..2708

( x i ) SEQUENCE DESCRIPTION: SEQ ID NO:3:

```
GGCCATTACC AATCGCGACC CGCGCACACA CGGCCCGGGC GGCGGGCGAA GCGGGCTCCC      60

GGGGCGCTGG GCGCAGGGCG CGGGGCAAGC CCCAGCAGCG TGTCTGCAAC GGGGCGCGGC     120

GGGCGCTCCA GCTCCGGGAT CTTTCTCCCT CGGTCACCTC CCTCGCGTCT AGGGAGGTCG     180

TGGCACTCCC TGAGGAGCGC GGCTGCTCGG AGGGCGGATC CTAGAACAGA GGCGTGAGAG     240

CCGGC ATG AAT GGT CAT ATG TCT AAC CGC TCC AGT GGG TAT GGA GTC          287
      Met Asn Gly His Met Ser Asn Arg Ser Ser Gly Tyr Gly Val
        1               5                  10

TAC CCT TCT CAA CTG AAT GGT TAC GGA TCT TCA CCA CCC TAT TCC CAG        335
Tyr Pro Ser Gln Leu Asn Gly Tyr Gly Ser Ser Pro Pro Tyr Ser Gln
 15                  20                  25                  30

ATG GAC AGA GAA CAC AGC TCA AGA ACA AGT GCA AAG GCC CTT TAT GAA        383
Met Asp Arg Glu His Ser Ser Arg Thr Ser Ala Lys Ala Leu Tyr Glu
                35                  40                  45

CAA AGG AAG AAC TAT GCC CGA GAC AGT GTC AGC AGT GTG TCG GAC GTG        431
Gln Arg Lys Asn Tyr Ala Arg Asp Ser Val Ser Ser Val Ser Asp Val
            50                  55                  60

TCC CAG TAC CGC GTG GAA CAC TTG ACC ACC TTC GTG CTG GAT CGG AAA        479
Ser Gln Tyr Arg Val Glu His Leu Thr Thr Phe Val Leu Asp Arg Lys
```

-continued

| | | | | | | | | | | | | | | | | |
|---|---|---|---|---|---|---|---|---|---|---|---|---|---|---|---|---|
| | | | 65 | | | | | 70 | | | | | 75 | | | |
| GAT | GCA | ATG | ATC | ACT | GTC | GAG | GAC | GGA | ATA | AGA | AAG | CTG | AAG | TTG | CTG | 527 |
| Asp | Ala | Met | Ile | Thr | Val | Glu | Asp | Gly | Ile | Arg | Lys | Leu | Lys | Leu | Leu | |
| | 80 | | | | | 85 | | | | | 90 | | | | | |
| GAT | GCC | AAG | GGC | AAA | GTG | TGG | ACT | CAA | GAT | ATG | ATT | CTC | CAA | GTG | GAT | 575 |
| Asp | Ala | Lys | Gly | Lys | Val | Trp | Thr | Gln | Asp | Met | Ile | Leu | Gln | Val | Asp | |
| 95 | | | | | 100 | | | | | 105 | | | | | 110 | |
| GAC | CGA | GCT | GTG | AGC | CTG | ATT | GAC | TTA | GAG | TCA | AAG | AAT | GAA | TTG | GAG | 623 |
| Asp | Arg | Ala | Val | Ser | Leu | Ile | Asp | Leu | Glu | Ser | Lys | Asn | Glu | Leu | Glu | |
| | | | | 115 | | | | | 120 | | | | | 125 | | |
| AAT | TTT | CCT | CTA | AAC | ACA | ATC | TCG | CAT | TGT | CAA | GCA | GTG | GTG | CAT | GCA | 671 |
| Asn | Phe | Pro | Leu | Asn | Thr | Ile | Ser | His | Cys | Gln | Ala | Val | Val | His | Ala | |
| | | | 130 | | | | | 135 | | | | | 140 | | | |
| TGC | AGC | TAT | GAC | TCC | ATT | CTC | GCC | TTG | GTA | TGC | AAA | GAG | CCA | ACG | CAG | 719 |
| Cys | Ser | Tyr | Asp | Ser | Ile | Leu | Ala | Leu | Val | Cys | Lys | Glu | Pro | Thr | Gln | |
| | | 145 | | | | | 150 | | | | | 155 | | | | |
| AGC | AAG | CCA | GAC | CTT | CAC | CTT | TTC | CAG | TGT | GAT | GAG | GTT | AAG | GCA | AAC | 767 |
| Ser | Lys | Pro | Asp | Leu | His | Leu | Phe | Gln | Cys | Asp | Glu | Val | Lys | Ala | Asn | |
| | 160 | | | | | 165 | | | | | 170 | | | | | |
| CTA | ATT | AGT | GAA | GAT | ATC | GAA | AGT | GCA | ATC | AGT | GAC | AGT | AAA | GGT | GGG | 815 |
| Leu | Ile | Ser | Glu | Asp | Ile | Glu | Ser | Ala | Ile | Ser | Asp | Ser | Lys | Gly | Gly | |
| 175 | | | | | 180 | | | | | 185 | | | | | 190 | |
| AAA | CAG | AAG | AGG | CGG | CCG | GAG | GCC | CTG | AGG | ATG | ATT | GCC | AAA | GCA | GAT | 863 |
| Lys | Gln | Lys | Arg | Arg | Pro | Glu | Ala | Leu | Arg | Met | Ile | Ala | Lys | Ala | Asp | |
| | | | | 195 | | | | | 200 | | | | | 205 | | |
| CCT | GGC | ATC | CCT | CCT | CCT | CCC | AGA | GCT | CCT | GCC | CCT | GTG | CCA | CCG | GGG | 911 |
| Pro | Gly | Ile | Pro | Pro | Pro | Pro | Arg | Ala | Pro | Ala | Pro | Val | Pro | Pro | Gly | |
| | | | 210 | | | | | 215 | | | | | 220 | | | |
| ACT | GTC | ACA | CAG | GTG | GAC | GTT | AGG | AGT | CGC | GTA | GCA | GCC | TGG | TCT | GCC | 959 |
| Thr | Val | Thr | Gln | Val | Asp | Val | Arg | Ser | Arg | Val | Ala | Ala | Trp | Ser | Ala | |
| | | 225 | | | | | 230 | | | | | 235 | | | | |
| TGG | GCA | GCT | GAC | CAG | GGT | GAC | TTC | GAG | AAG | CCC | CGG | CAG | TAC | CAC | GAG | 1007 |
| Trp | Ala | Ala | Asp | Gln | Gly | Asp | Phe | Glu | Lys | Pro | Arg | Gln | Tyr | His | Glu | |
| | 240 | | | | | 245 | | | | | 250 | | | | | |
| CAA | GAA | GAG | ACG | CCC | GAG | ATG | ATG | GCA | GCC | CGG | ATC | GAC | AGG | GAT | GTG | 1055 |
| Gln | Glu | Glu | Thr | Pro | Glu | Met | Met | Ala | Ala | Arg | Ile | Asp | Arg | Asp | Val | |
| 255 | | | | | 260 | | | | | 265 | | | | | 270 | |
| CAA | ATC | TTA | AAC | CAT | ATT | TTG | GAT | GAC | ATT | GAA | TTT | TTT | ATC | ACC | AAA | 1103 |
| Gln | Ile | Leu | Asn | His | Ile | Leu | Asp | Asp | Ile | Glu | Phe | Phe | Ile | Thr | Lys | |
| | | | | 275 | | | | | 280 | | | | | 285 | | |
| CTC | CAA | AAA | GCC | GCC | GAA | GCG | TTT | TCT | GAG | CTT | TCT | AAA | AGG | AAG | AAA | 1151 |
| Leu | Gln | Lys | Ala | Ala | Glu | Ala | Phe | Ser | Glu | Leu | Ser | Lys | Arg | Lys | Lys | |
| | | | 290 | | | | | 295 | | | | | 300 | | | |
| AGT | AAG | AAA | AGT | AAA | AGG | AAA | GGA | CCT | GGA | GAG | GGC | GTT | TTA | ACA | CTG | 1199 |
| Ser | Lys | Lys | Ser | Lys | Arg | Lys | Gly | Pro | Gly | Glu | Gly | Val | Leu | Thr | Leu | |
| | | 305 | | | | | 310 | | | | | 315 | | | | |
| AGG | GCA | AAA | CCG | CCA | CCT | CCT | GAC | GAG | TTT | GTT | GAC | TGT | TTC | CAG | AAG | 1247 |
| Arg | Ala | Lys | Pro | Pro | Pro | Pro | Asp | Glu | Phe | Val | Asp | Cys | Phe | Gln | Lys | |
| | 320 | | | | | 325 | | | | | 330 | | | | | |
| TTT | AAA | CAT | GGA | TTC | AAC | CTT | CTG | GCC | AAG | TTG | AAG | TCC | CAT | ATC | CAG | 1295 |
| Phe | Lys | His | Gly | Phe | Asn | Leu | Leu | Ala | Lys | Leu | Lys | Ser | His | Ile | Gln | |
| 335 | | | | | 340 | | | | | 345 | | | | | 350 | |
| AAC | CCG | AGT | GCT | TCA | GAT | CTG | GTT | CAT | TTT | TTG | TTT | ACT | CCA | CTA | AAT | 1343 |
| Asn | Pro | Ser | Ala | Ser | Asp | Leu | Val | His | Phe | Leu | Phe | Thr | Pro | Leu | Asn | |
| | | | | 355 | | | | | 360 | | | | | 365 | | |
| ATG | GTG | GTC | CAG | GCA | ACA | GGT | GGC | CCT | GAA | CTG | GCC | AGT | TCG | GTA | CTC | 1391 |
| Met | Val | Val | Gln | Ala | Thr | Gly | Gly | Pro | Glu | Leu | Ala | Ser | Ser | Val | Leu | |
| | | | 370 | | | | | 375 | | | | | 380 | | | |
| AGC | CCA | CTG | TTG | ACA | AAA | GAC | ACA | GTT | GAT | TTC | TTA | AAC | TAC | ACA | GCC | 1439 |
| Ser | Pro | Leu | Leu | Thr | Lys | Asp | Thr | Val | Asp | Phe | Leu | Asn | Tyr | Thr | Ala | |

|  |  |  |  |  |  |  |  |  |  |  |  |  |  |  |  |  |
|---|---|---|---|---|---|---|---|---|---|---|---|---|---|---|---|---|
|  |  | 385 |  |  |  |  |  | 390 |  |  |  |  |  | 395 |  |  |
| ACT | GCG | GAG | GAA | CGG | AAG | CTG | TGG | ATG | TCA | CTG | GGA | GAT | AGT | TGG | GTG | 1487 |
| Thr | Ala | Glu | Glu | Arg | Lys | Leu | Trp | Met | Ser | Leu | Gly | Asp | Ser | Trp | Val |  |
|  | 400 |  |  |  | 405 |  |  |  |  | 410 |  |  |  |  |  |  |
| AAA | GTG | AGA | GCA | GAG | TGG | CCG | AAA | GAA | CAG | TTC | ATC | CCA | CCT | TAC | GTC | 1535 |
| Lys | Val | Arg | Ala | Glu | Trp | Pro | Lys | Glu | Gln | Phe | Ile | Pro | Pro | Tyr | Val |  |
| 415 |  |  |  |  | 420 |  |  |  |  | 425 |  |  |  |  | 430 |  |
| CCG | AGG | TTC | CGC | AAC | GGC | TGG | GAG | CCC | CCG | ATG | CTG | AAC | TTC | ATG | GGC | 1583 |
| Pro | Arg | Phe | Arg | Asn | Gly | Trp | Glu | Pro | Pro | Met | Leu | Asn | Phe | Met | Gly |  |
|  |  |  |  | 435 |  |  |  |  | 440 |  |  |  |  | 445 |  |  |
| GCG | CCC | ACA | GAG | CAA | GAC | ATG | TAT | CAA | CTG | GCC | GAG | TCC | GTG | GCC | AAC | 1631 |
| Ala | Pro | Thr | Glu | Gln | Asp | Met | Tyr | Gln | Leu | Ala | Glu | Ser | Val | Ala | Asn |  |
|  |  |  | 450 |  |  |  |  | 455 |  |  |  | 460 |  |  |  |  |
| GCA | GAA | CAC | CAG | CGC | AAA | CAG | GAC | AGC | AAG | AGG | CTG | TCC | ACA | GAG | CAT | 1679 |
| Ala | Glu | His | Gln | Arg | Lys | Gln | Asp | Ser | Lys | Arg | Leu | Ser | Thr | Glu | His |  |
|  |  | 465 |  |  |  |  | 470 |  |  |  |  | 475 |  |  |  |  |
| TCC | AAT | GTG | TCC | GAC | TAT | CCT | CCA | GCC | GAC | GGA | TAT | GCG | TAC | AGT | AGC | 1727 |
| Ser | Asn | Val | Ser | Asp | Tyr | Pro | Pro | Ala | Asp | Gly | Tyr | Ala | Tyr | Ser | Ser |  |
|  | 480 |  |  |  |  | 485 |  |  |  |  | 490 |  |  |  |  |  |
| AGC | ATG | TAC | CAC | AGA | GGA | CCA | CAT | GCA | GAC | CAC | GGG | GAG | GCT | GCC | ATG | 1775 |
| Ser | Met | Tyr | His | Arg | Gly | Pro | His | Ala | Asp | His | Gly | Glu | Ala | Ala | Met |  |
| 495 |  |  |  |  | 500 |  |  |  |  | 505 |  |  |  |  | 510 |  |
| CCT | TTC | AAG | TCA | ACT | CCT | AAT | CAC | CAA | GTA | GAT | AGG | AAT | TAT | GAC | GCA | 1823 |
| Pro | Phe | Lys | Ser | Thr | Pro | Asn | His | Gln | Val | Asp | Arg | Asn | Tyr | Asp | Ala |  |
|  |  |  |  | 515 |  |  |  |  | 520 |  |  |  |  | 525 |  |  |
| GTC | AAA | ACA | CAA | CCC | AAG | AAA | TAC | GCC | AAA | TCC | AAG | TAC | GAC | TTT | GTG | 1871 |
| Val | Lys | Thr | Gln | Pro | Lys | Lys | Tyr | Ala | Lys | Ser | Lys | Tyr | Asp | Phe | Val |  |
|  |  |  | 530 |  |  |  |  | 535 |  |  |  | 540 |  |  |  |  |
| GCG | AGG | AAC | AGC | AGC | GAG | CTC | TCG | GTT | ATG | AAA | GAT | GAT | GTC | TTA | GAG | 1919 |
| Ala | Arg | Asn | Ser | Ser | Glu | Leu | Ser | Val | Met | Lys | Asp | Asp | Val | Leu | Glu |  |
|  |  | 545 |  |  |  |  | 550 |  |  |  |  | 555 |  |  |  |  |
| ATA | CTC | GAC | GAT | CGA | AGG | CAG | TGG | TGG | AAA | GTC | CGG | AAT | GCC | AGT | GGA | 1967 |
| Ile | Leu | Asp | Asp | Arg | Arg | Gln | Trp | Trp | Lys | Val | Arg | Asn | Ala | Ser | Gly |  |
|  | 560 |  |  |  |  | 565 |  |  |  |  | 570 |  |  |  |  |  |
| GAC | TCT | GGG | TTT | GTG | CCA | AAT | AAC | ATT | CTG | GAT | ATC | ATG | AGA | ACT | CCA | 2015 |
| Asp | Ser | Gly | Phe | Val | Pro | Asn | Asn | Ile | Leu | Asp | Ile | Met | Arg | Thr | Pro |  |
| 575 |  |  |  |  | 580 |  |  |  |  | 585 |  |  |  |  | 590 |  |
| GAA | TCT | GGA | GTG | GGG | CGC | GCT | GAC | CCC | CCA | TAC | ACA | CAT | ACC | ATA | CAG | 2063 |
| Glu | Ser | Gly | Val | Gly | Arg | Ala | Asp | Pro | Pro | Tyr | Thr | His | Thr | Ile | Gln |  |
|  |  |  |  | 595 |  |  |  |  | 600 |  |  |  |  | 605 |  |  |
| AAA | CAA | AGG | ACG | GAA | TAC | GGC | CTG | AGA | TCA | GCT | GAC | ACT | CCT | TCT | GCC | 2111 |
| Lys | Gln | Arg | Thr | Glu | Tyr | Gly | Leu | Arg | Ser | Ala | Asp | Thr | Pro | Ser | Ala |  |
|  |  |  | 610 |  |  |  |  | 615 |  |  |  | 620 |  |  |  |  |
| CCA | TCA | CCC | CCT | CCA | ACG | CCA | GCA | CCC | GTT | CCG | GTC | CCC | CTT | CCA | CCT | 2159 |
| Pro | Ser | Pro | Pro | Pro | Thr | Pro | Ala | Pro | Val | Pro | Val | Pro | Leu | Pro | Pro |  |
|  |  | 625 |  |  |  |  | 630 |  |  |  |  | 635 |  |  |  |  |
| TCT | GTA | CCA | GCA | CCC | GTT | TCT | GTG | CCC | AAG | GTT | CCA | GCA | GAT | GTC | ACC | 2207 |
| Ser | Val | Pro | Ala | Pro | Val | Ser | Val | Pro | Lys | Val | Pro | Ala | Asp | Val | Thr |  |
|  | 640 |  |  |  |  | 645 |  |  |  |  | 650 |  |  |  |  |  |
| CGC | CAG | AAC | AGC | AGC | TCC | AGT | GAC | AGT | GGG | GGC | AGC | ATT | GTG | CGG | GAC | 2255 |
| Arg | Gln | Asn | Ser | Ser | Ser | Ser | Asp | Ser | Gly | Gly | Ser | Ile | Val | Arg | Asp |  |
| 655 |  |  |  |  | 660 |  |  |  |  | 665 |  |  |  |  | 670 |  |
| AGC | CAG | AGA | TAC | AAA | CAA | CTC | CCA | GTG | GAC | CGA | AGG | AAG | TCC | CAG | ATG | 2303 |
| Ser | Gln | Arg | Tyr | Lys | Gln | Leu | Pro | Val | Asp | Arg | Arg | Lys | Ser | Gln | Met |  |
|  |  |  |  | 675 |  |  |  |  | 680 |  |  |  |  | 685 |  |  |
| GAA | GAG | GTT | CAG | GAT | GAG | CTC | TTC | CAG | AGG | CTG | ACC | ATC | GGG | CGC | AGT | 2351 |
| Glu | Glu | Val | Gln | Asp | Glu | Leu | Phe | Gln | Arg | Leu | Thr | Ile | Gly | Arg | Ser |  |
|  |  |  | 690 |  |  |  |  | 695 |  |  |  | 700 |  |  |  |  |
| GCT | GCG | CAG | AGG | AAG | TTC | CAC | GTG | CCA | CGG | CAG | AAC | GTT | CCA | GTG | ATC | 2399 |
| Ala | Ala | Gln | Arg | Lys | Phe | His | Val | Pro | Arg | Gln | Asn | Val | Pro | Val | Ile |  |

|     | 705 |     |     |     | 710 |     |     |     |     | 715 |     |     |     |     |      |
| --- | --- | --- | --- | --- | --- | --- | --- | --- | --- | --- | --- | --- | --- | --- | ---- |
| AAT | ATC | ACT | TAT | GAC | TCC | TCA | CCG | GAA | GAA | GTA | AAG | ACT | TGG | CTG | CAG  | 2447 |
| Asn | Ile | Thr | Tyr | Asp | Ser | Ser | Pro | Glu | Glu | Val | Lys | Thr | Trp | Leu | Gln  |
|     | 720 |     |     |     | 725 |     |     |     |     | 730 |     |     |     |     |      |
| TCA | AAG | GGA | TTC | AAT | CCC | GTG | ACT | GTC | AAT | AGC | CTC | GGG | GTG | TTG | AAC  | 2495 |
| Ser | Lys | Gly | Phe | Asn | Pro | Val | Thr | Val | Asn | Ser | Leu | Gly | Val | Leu | Asn  |
| 735 |     |     |     |     | 740 |     |     |     |     | 745 |     |     |     |     | 750  |
| GGA | GCA | CAA | CTC | TTT | TCT | CTC | AAC | AAA | GAC | GAA | CTG | AGG | TCT | GTC | TGC  | 2543 |
| Gly | Ala | Gln | Leu | Phe | Ser | Leu | Asn | Lys | Asp | Glu | Leu | Arg | Ser | Val | Cys  |
|     |     |     |     | 755 |     |     |     |     | 760 |     |     |     |     | 765 |      |
| CCG | GAA | GGT | GCC | AGA | GTC | TTT | AAC | CAA | ATC | ACT | GTT | CAG | AAA | GCT | GCT  | 2591 |
| Pro | Glu | Gly | Ala | Arg | Val | Phe | Asn | Gln | Ile | Thr | Val | Gln | Lys | Ala | Ala  |
|     |     |     | 770 |     |     |     |     | 775 |     |     |     |     | 780 |     |      |
| TTG | GAG | GAC | AGT | AAT | GGA | AGC | TCC | GAG | TTA | CAA | GAG | ATC | ATG | CGG | AGA  | 2639 |
| Leu | Glu | Asp | Ser | Asn | Gly | Ser | Ser | Glu | Leu | Gln | Glu | Ile | Met | Arg | Arg  |
|     |     | 785 |     |     |     |     | 790 |     |     |     |     | 795 |     |     |      |
| CGG | CAG | GAG | AAG | ATC | AGC | GCC | GCT | GCG | AGC | GAC | TCG | GGA | GTG | GAG | TCT  | 2687 |
| Arg | Gln | Glu | Lys | Ile | Ser | Ala | Ala | Ala | Ser | Asp | Ser | Gly | Val | Glu | Ser  |
|     |     | 800 |     |     |     |     | 805 |     |     |     |     | 810 |     |     |      |
| TTT | GAT | GAA | GGG | AGC | AGC | CAC | TGAGTCCATG AACTTCCTTA TTCTTGGTGT        | 2738 |
| Phe | Asp | Glu | Gly | Ser | Ser | His |                                         |
| 815 |     |     |     |     | 820 |     |                                         |

| GGTCGTTGAA | CAGTGATGGA | CATGCTTTGT | TTTAAGAAGC | CTTGAAGGGA | ATGTCAAAGC | 2798 |
| TGTCGTCTTG | GTATATGTAA | TTTATCGCCA | TATAAGGAAA | CAGTATATGC | CTGAGTAAGC | 2858 |
| AGAGGACCCG | CTGCTTCTGT | GCACATTAGT | TTGATTAAAA | CTGAGAAGCG | GGTAGGTGAG | 2918 |
| ATGGCTCAGC | AAGTAAAGGT | GCTTGCTGCC | AAGCCCAATG | ACCCAAGTTC | GAGTCCCTGG | 2978 |
| GTCTACATGG | TAGGAGAGAG | CTGGCTTCTG | CAAGTTGTCC | TCTGACCACC | ACACATAAAT | 3038 |
| AAATAACAAA | TGTAATTTAC | AAACTTTTAA | AAGAAAATGT | AATTTAAAAA | ACCAGACGTT | 3098 |
| CTAGACTGTT | CTGGGCTTGG | GAAATATTTT | TTTCACTTTC | CTAAGGTGTA | CTTTCCTTTG | 3158 |
| CTACATTAAT | TATTGCAGCC | TTGTTCGATG | ATCTAAGTGG | GGATATTTGA | CAATGGCAGA | 3218 |
| TTTATTCATT | GCAACAAGGA | AAGACAC    |            |            |            | 3245 |

( 2 ) INFORMATION FOR SEQ ID NO:4:

( i ) SEQUENCE CHARACTERISTICS:
        ( A ) LENGTH: 821 amino acids
        ( B ) TYPE: amino acid
        ( D ) TOPOLOGY: linear ( ii ) MOLECULE TYPE: protein ( x i ) SEQUENCE DESCRIPTION: SEQ ID NO:4:

| Met | Asn | Gly | His | Met | Ser | Asn | Arg | Ser | Ser | Gly | Tyr | Gly | Val | Tyr | Pro |
| 1   |     |     |     | 5   |     |     |     |     | 10  |     |     |     |     | 15  |     |
| Ser | Gln | Leu | Asn | Gly | Tyr | Gly | Ser | Ser | Pro | Pro | Tyr | Ser | Gln | Met | Asp |
|     |     |     | 20  |     |     |     | 25  |     |     |     |     |     | 30  |     |     |
| Arg | Glu | His | Ser | Ser | Arg | Thr | Ser | Ala | Lys | Ala | Leu | Tyr | Glu | Gln | Arg |
|     |     | 35  |     |     |     |     | 40  |     |     |     |     | 45  |     |     |     |
| Lys | Asn | Tyr | Ala | Arg | Asp | Ser | Val | Ser | Ser | Val | Ser | Asp | Val | Ser | Gln |
|     | 50  |     |     |     |     | 55  |     |     |     |     | 60  |     |     |     |     |
| Tyr | Arg | Val | Glu | His | Leu | Thr | Thr | Phe | Val | Leu | Asp | Arg | Lys | Asp | Ala |
| 65  |     |     |     |     | 70  |     |     |     |     | 75  |     |     |     |     | 80  |
| Met | Ile | Thr | Val | Glu | Asp | Gly | Ile | Arg | Lys | Leu | Lys | Leu | Leu | Asp | Ala |
|     |     |     |     | 85  |     |     |     |     | 90  |     |     |     |     | 95  |     |
| Lys | Gly | Lys | Val | Trp | Thr | Gln | Asp | Met | Ile | Leu | Gln | Val | Asp | Arg |     |
|     |     |     | 100 |     |     |     |     | 105 |     |     |     |     | 110 |     |     |

```
Ala  Val  Ser  Leu  Ile  Asp  Leu  Glu  Ser  Lys  Asn  Glu  Leu  Glu  Asn  Phe
          115            120                      125

Pro  Leu  Asn  Thr  Ile  Ser  His  Cys  Gln  Ala  Val  Val  His  Ala  Cys  Ser
          130            135                      140

Tyr  Asp  Ser  Ile  Leu  Ala  Leu  Val  Cys  Lys  Glu  Pro  Thr  Gln  Ser  Lys
145                      150                 155                           160

Pro  Asp  Leu  His  Leu  Phe  Gln  Cys  Asp  Glu  Val  Lys  Ala  Asn  Leu  Ile
               165                      170                           175

Ser  Glu  Asp  Ile  Glu  Ser  Ala  Ile  Ser  Asp  Ser  Lys  Gly  Lys  Gln
               180                 185                      190

Lys  Arg  Arg  Pro  Glu  Ala  Leu  Arg  Met  Ile  Ala  Lys  Ala  Asp  Pro  Gly
          195                      200                      205

Ile  Pro  Pro  Pro  Pro  Arg  Ala  Pro  Ala  Pro  Val  Pro  Pro  Gly  Thr  Val
     210                 215                      220

Thr  Gln  Val  Asp  Val  Arg  Ser  Arg  Val  Ala  Ala  Trp  Ser  Ala  Trp  Ala
225                      230                 235                           240

Ala  Asp  Gln  Gly  Asp  Phe  Glu  Lys  Pro  Arg  Gln  Tyr  His  Glu  Gln  Glu
               245                      250                      255

Glu  Thr  Pro  Glu  Met  Met  Ala  Ala  Arg  Ile  Asp  Arg  Asp  Val  Gln  Ile
               260                 265                      270

Leu  Asn  His  Ile  Leu  Asp  Asp  Ile  Glu  Phe  Phe  Ile  Thr  Lys  Leu  Gln
          275                      280                      285

Lys  Ala  Ala  Glu  Ala  Phe  Ser  Glu  Leu  Ser  Lys  Arg  Lys  Lys  Ser  Lys
     290                      295                 300

Lys  Ser  Lys  Arg  Lys  Gly  Pro  Gly  Glu  Gly  Val  Leu  Thr  Leu  Arg  Ala
305                      310                 315                           320

Lys  Pro  Pro  Pro  Pro  Asp  Glu  Phe  Val  Asp  Cys  Phe  Gln  Lys  Phe  Lys
               325                      330                      335

His  Gly  Phe  Asn  Leu  Leu  Ala  Lys  Leu  Lys  Ser  His  Ile  Gln  Asn  Pro
               340                 345                      350

Ser  Ala  Ser  Asp  Leu  Val  His  Phe  Leu  Phe  Thr  Pro  Leu  Asn  Met  Val
          355                      360                      365

Val  Gln  Ala  Thr  Gly  Gly  Pro  Glu  Leu  Ala  Ser  Ser  Val  Leu  Ser  Pro
     370                      375                 380

Leu  Leu  Thr  Lys  Asp  Thr  Val  Asp  Phe  Leu  Asn  Tyr  Thr  Ala  Thr  Ala
385                      390                 395                           400

Glu  Glu  Arg  Lys  Leu  Trp  Met  Ser  Leu  Gly  Asp  Ser  Trp  Val  Lys  Val
               405                      410                      415

Arg  Ala  Glu  Trp  Pro  Lys  Glu  Gln  Phe  Ile  Pro  Pro  Tyr  Val  Pro  Arg
               420                      425                      430

Phe  Arg  Asn  Gly  Trp  Glu  Pro  Pro  Met  Leu  Asn  Phe  Met  Gly  Ala  Pro
          435                      440                      445

Thr  Glu  Gln  Asp  Met  Tyr  Gln  Leu  Ala  Glu  Ser  Val  Ala  Asn  Ala  Glu
     450                      455                 460

His  Gln  Arg  Lys  Gln  Asp  Ser  Lys  Arg  Leu  Ser  Thr  Glu  His  Ser  Asn
465                      470                 475                           480

Val  Ser  Asp  Tyr  Pro  Pro  Ala  Asp  Gly  Tyr  Ala  Tyr  Ser  Ser  Ser  Met
               485                      490                      495

Tyr  His  Arg  Gly  Pro  His  Ala  Asp  His  Gly  Glu  Ala  Ala  Met  Pro  Phe
               500                      505                      510

Lys  Ser  Thr  Pro  Asn  His  Gln  Val  Asp  Arg  Asn  Tyr  Asp  Ala  Val  Lys
          515                      520                      525

Thr  Gln  Pro  Lys  Lys  Tyr  Ala  Lys  Ser  Lys  Tyr  Asp  Phe  Val  Ala  Arg
```

|          |          |          |          | 530      |          |          |          |          | 535      |          |          |          |          | 540      |          |          |          |
|----------|----------|----------|----------|----------|----------|----------|----------|----------|----------|----------|----------|----------|----------|----------|----------|----------|----------|

Asn Ser Ser Glu Leu Ser Val Met Lys Asp Asp Val Leu Glu Ile Leu
545                     550                 555                 560

Asp Asp Arg Arg Gln Trp Trp Lys Val Arg Asn Ala Ser Gly Asp Ser
                565                 570                 575

Gly Phe Val Pro Asn Asn Ile Leu Asp Ile Met Arg Thr Pro Glu Ser
            580                 585                 590

Gly Val Gly Arg Ala Asp Pro Pro Tyr Thr His Thr Ile Gln Lys Gln
            595                 600                 605

Arg Thr Glu Tyr Gly Leu Arg Ser Ala Asp Thr Pro Ser Ala Pro Ser
    610                 615                 620

Pro Pro Pro Thr Pro Ala Pro Val Pro Val Pro Leu Pro Pro Ser Val
625                 630                 635                 640

Pro Ala Pro Val Ser Val Pro Lys Val Pro Ala Asp Val Thr Arg Gln
                645                 650                 655

Asn Ser Ser Ser Ser Asp Ser Gly Gly Ser Ile Val Arg Asp Ser Gln
            660                 665                 670

Arg Tyr Lys Gln Leu Pro Val Asp Arg Arg Lys Ser Gln Met Glu Glu
        675                 680                 685

Val Gln Asp Glu Leu Phe Gln Arg Leu Thr Ile Gly Arg Ser Ala Ala
    690                 695                 700

Gln Arg Lys Phe His Val Pro Arg Gln Asn Val Pro Val Ile Asn Ile
705                 710                 715                 720

Thr Tyr Asp Ser Ser Pro Glu Glu Val Lys Thr Trp Leu Gln Ser Lys
                725                 730                 735

Gly Phe Asn Pro Val Thr Val Asn Ser Leu Gly Val Leu Asn Gly Ala
            740                 745                 750

Gln Leu Phe Ser Leu Asn Lys Asp Glu Leu Arg Ser Val Cys Pro Glu
        755                 760                 765

Gly Ala Arg Val Phe Asn Gln Ile Thr Val Gln Lys Ala Ala Leu Glu
    770                 775                 780

Asp Ser Asn Gly Ser Ser Glu Leu Gln Glu Ile Met Arg Arg Arg Gln
785                 790                 795                 800

Glu Lys Ile Ser Ala Ala Ala Ser Asp Ser Gly Val Glu Ser Phe Asp
                805                 810                 815

Glu Gly Ser Ser His
            820

( 2 ) INFORMATION FOR SEQ ID NO:5:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:5:

CGAGCTCGAG AGATCAGCTG ACACTCCTTC T        31

( 2 ) INFORMATION FOR SEQ ID NO:6:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:6:

CGATATCGAT TCTCTTGTAA CTCGGAGCTT C          31